US008088365B2

(12) United States Patent
Harris

(10) Patent No.: US 8,088,365 B2
(45) **Date of Patent: *Jan. 3, 2012**

(54) SOLUBLE, DEGRADABLE POLY(ETHYLENE GLYCOL) DERIVATIVES FOR CONTROLLABLE RELEASE OF BOUND MOLECULES INTO SOLUTION

(75) Inventor: J. Milton Harris, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 12/414,621

(22) Filed: Mar. 30, 2009

(65) Prior Publication Data

US 2009/0215988 A1 Aug. 27, 2009

Related U.S. Application Data

(60) Continuation of application No. 11/051,728, filed on Feb. 4, 2005, now Pat. No. 7,655,747, which is a continuation of application No. 10/318,322, filed on Dec. 12, 2002, now Pat. No. 6,864,350, which is a continuation of application No. 09/824,297, filed on Apr. 2, 2001, now Pat. No. 6,515,100, which is a division of application No. 08/937,846, filed on Sep. 25, 1997, now Pat. No. 6,214,966.

(60) Provisional application No. 60/026,716, filed on Sep. 26, 1996.

(51) Int. Cl.
*A61K 31/74* (2006.01)
*A61K 31/00* (2006.01)
*A61K 31/765* (2006.01)
*C08G 73/10* (2006.01)

(52) U.S. Cl. .................... 424/78.08; 424/17; 424/78.19; 424/78.33; 528/322

(58) Field of Classification Search ............... 424/78.08, 424/78.17, 78.19, 78.33; 528/322
See application file for complete search history.

(56) References Cited

U.S. PATENT DOCUMENTS 4,179,337 A 12/1979 Davis et al.
(Continued)

FOREIGN PATENT DOCUMENTS

WO 95/11924 5/1995
(Continued)

OTHER PUBLICATIONS

Greenwald, et al., "Highly Water Soluble Taxol Derivatives; 7-Polyethylene Glycol Carbamates and Carbonates", J. Org. Chem., vol. 60, No. 2, pp. 331-336, (1995).

(Continued)

*Primary Examiner* — Blessing Fubara
(74) *Attorney, Agent, or Firm* — Mark A. Wilson

(57) ABSTRACT

PEG and related polymer derivatives having weak, hydrolytically unstable linkages near the reactive end of the polymer are provided for conjugation to drugs, including proteins, enzymes, small molecules, and others. These derivatives provide a sufficient circulation period for a drug-PEG conjugate, followed by hydrolytic breakdown of the conjugate and release of the bound molecule. In some cases, drugs that demonstrate reduced activity when permanently coupled to PEG maintain a therapeutically suitable activity when coupled to a degradable PEG in accordance with the invention. The PEG derivatives of the invention can be used to impart improved water solubility, increased size, a slower rate of kidney clearance, and reduced immunogenicity to a conjugate formed by attachment thereto. Controlled hydrolytic release of the bound molecule into an aqueous environment can then enhance the drug's delivery profile by providing a delivery system which employs such polymers and utilizes the teachings provided herein.

9 Claims, 3 Drawing Sheets

27508.8
30531.0
33518.4
36575.6
28000
32000
36000
40000
MASS (m/Z)

U.S. PATENT DOCUMENTS

| | | | | |
|---|---|---|---|---|
| 4,670,417 | A | 6/1987 | Iwasaki et al. | |
| 4,766,106 | A | 8/1988 | Katre et al. | |
| 5,476,653 | A | 12/1995 | Pitt et al. | |
| 5,672,662 | A | 9/1997 | Harris et al. | |
| 5,720,950 | A | 2/1998 | Poiani et al. | |
| 5,730,990 | A | 3/1998 | Greenwald et al. | |
| 5,738,846 | A | 4/1998 | Greenwald et al. | |
| 5,840,900 | A | 11/1998 | Greenwald et al. | |
| 6,214,966 | B1 * | 4/2001 | Harris | 528/322 |
| 6,515,100 | B2 * | 2/2003 | Harris | 528/322 |
| 6,864,350 | B2 * | 3/2005 | Harris | 528/322 |
| 7,655,747 | B2 * | 2/2010 | Harris | 528/322 |
| 2005/0158273 | A1 | 7/2005 | Harris | |
| 2005/0171328 | A1 | 8/2005 | Harris | |

FOREIGN PATENT DOCUMENTS

| | | | |
|---|---|---|---|
| WO | WO 95/11924 | * | 5/1995 |
| WO | 96/21469 | | 7/1996 |

OTHER PUBLICATIONS

Harris, "Introduction to Biotechnical and Biomedical Applications of Poly(Ethylene Glycol)", Poly(Ethylene Glycol) Chemistry: Biotechnical and Biomedical Applications, Plenum New York, pp. 1-14, (1992).

Torchilin, et al., "Amphiphilic Polyethylene Glycol Derivatives: Long-Circulating Micellar Carriers for Therapeutic and Diagnostic Agents", Polymer Preprints, vol. 38, No. 1, pp. 545-546, (1997).

Zalipsky, et al., "Attachment of Drugs to Polyethylene Glycols", European Polymer Journal, vol, 19, No. 12, pp. 1177-1183.(1983).

Shearwater Polymers, Inc., Polyethylene Glycol and Derivatives, Catalog, pp. 2-53, (1997-1998).

Shearwater Polymers, Inc., Catalog, pp. 2-49, (1995).

* cited by examiner

SOLUBLE, DEGRADABLE POLY(ETHYLENE GLYCOL) DERIVATIVES FOR CONTROLLABLE RELEASE OF BOUND MOLECULES INTO SOLUTION

CROSS REFERENCE TO RELATED APPLICATIONS

This application is a continuation of U.S. patent application Ser. No. 11/051,728, filed Feb. 4, 2005, which is a continuation of U.S. patent application Ser. No. 10/318,322, filed Dec. 12, 2002, now U.S. Pat. No. 6,864,350, which is a continuation of U.S. patent application Ser. No. 09/824,297, filed Apr. 2, 2001, now U.S. Pat. No. 6,515,100, which is a divisional of U.S. patent application Ser. No. 08/937,846, filed Sep. 25, 1997, now U.S. Pat. No. 6,214,966, which claims the benefit of priority to Provisional Patent Application Ser. No. 60/026,716, filed Sep. 26, 1996, the contents of which are all incorporated herein by reference in their entireties.

FIELD OF THE INVENTION

This invention relates to active derivatives of poly(ethylene glycol) and related hydrophilic polymers having a reactive moiety at one end of the polymer chain suitable for chemical coupling to another molecule.

BACKGROUND OF THE INVENTION

Chemical attachment of the hydrophilic polymer poly(ethylene glycol)(PEG), which is also known as poly(ethylene oxide) (PEO), to molecules and surfaces is of great utility in biotechnology. In its most common form PEG is a linear polymer terminated at each end with a hydroxyl group:

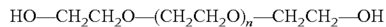

$$HO—CH_2CH_2O—(CH_2CH_2O)_n—CH_2CH_2—OH$$

This polymer can be represented in brief form as "HO-PEG-OH" where it is understood that the -PEG- symbol represents the following structural unit:

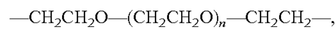

$$—CH_2CH_2O—(CH_2CH_2O)_n—CH_2CH_2—,$$

where n typically ranges from approximately 10 to approximately 2000.

PEG is commonly used as methoxy-PEG-OH, or "mPEG", in which one terminus is the relatively inert methoxy group, while the other terminus is a hydroxyl group that is subject to ready chemical modification.

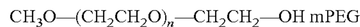

$$CH_3O—(CH_2CH_2O)_n—CH_2CH_2—OH \text{ mPEG}$$

PEG is also commonly used in branched forms that can be prepared by addition of ethylene oxide to various polyols, such as glycerol, pentaerythritol and sorbitol. For example, the four-arm, branched PEG prepared from pentaerythritol is shown below:

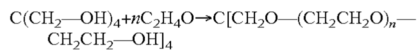

$$C(CH_2—OH)_4+nC_2H_4O \rightarrow C[CH_2O—(CH_2CH_2O)_n—CH_2CH_2—OH]_4$$

Such branched polyethylene glycols can be represented in general form as $R(\text{-PEG-OH})_z$ in which R represents the central "core" molecule, such as glycerol or pentaerythritol, and z represents the number of arms extending therefrom.

PEG is a well-known polymer having the following properties: solubility in water and in many organic solvents, lack of toxicity, and lack of immunogenicity. One use of PEG is to covalently attach the polymer to insoluble molecules to make the resulting PEG-molecule conjugate soluble. For example, Greenwald, Pendri and Bolikal in *J. Org. Chem.,* 60, 331-336 (1995), have shown that the water-insoluble drug, taxol, when coupled to PEG, becomes water-soluble.

In related work, Davis et al., in U.S. Pat. No. 4,179,337, have shown that proteins coupled to PEG have enhanced blood-circulation lifetimes due to reduced rate of kidney clearance and reduced immunogenicity. Hydrophobic proteins have been described that, upon coupling to PEG, have increased solubility in water. These and other uses for PEG are described in J. M. Harris, Ed., "*Biomedical and Biotechnical Applications of Polyethylene Glycol Chemistry*," Plenum, New York, 1992).

To couple PEG to a molecule such as a protein or onto a surface, it is necessary to use an "activated derivative" of the PEG having a functional group at a terminus suitable for reacting with some group on the protein or on the surface (such as an amino group). Among the many useful activated derivatives of PEG is the succinimidyl "active ester" of carboxymethylated PEG as disclosed by K. Iwasaki and Y. Iwashita in U.S. Pat. No. 4,670,417. This chemistry can be illustrated with the active ester reacting with amino groups of a protein (the succinimidyl group is represented as "NHS" and the amino-containing protein is represented as PRO-$NH_2$):

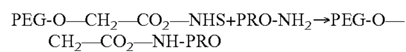

$$\text{PEG-O—}CH_2—CO_2\text{—NHS+PRO-}NH_2 \rightarrow \text{PEG-O—}CH_2—CO_2\text{—NH-PRO}$$

Certain problems have arisen in the art. Some of the functional groups that have been used to activate PEG can result in toxic or otherwise undesirable residues when used for in vivo drug delivery. Some of the linkages that have been devised to attach functional groups to PEG can result in an undesirable immune response. Additionally, certain functional groups do not have appropriate selectivity for reacting with particular groups on proteins and can deactivate the proteins when in conjugated form.

Attachment of a PEG derivative to a substance can have a somewhat unpredictable impact on the substance. Proteins, small drugs, and the like may have reduced biological activity when conjugated to a PEG derivative, although in some cases, activity may be increased.

Another example of a problem that has arisen in the art is exemplified by the succinimidyl succinate active ester, "mPEG-SS" (the succinimidyl group is represented as NHS):

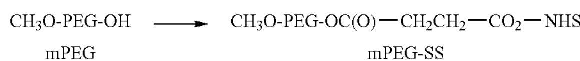

$$\underset{\text{mPEG}}{CH_3O\text{-PEG-OH}} \longrightarrow \underset{\text{mPEG-SS}}{CH_3O\text{-PEG-OC(O)}—CH_2CH_2—CO_2—\text{NHS}}$$

The mPEG-SS active ester is useful for coupling because it reacts rapidly with amino groups on proteins and other molecules to form an amide linkage (—CO—NH—). A problem has been reported with the mPEG-SS active ester, as noted in U.S. Pat. No. 4,670,417. Since this compound possesses an ester linkage in the backbone that remains after coupling to an amine group, such as in a protein (represented as PRO-$NH_2$):

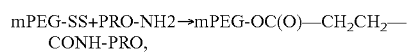

$$\text{mPEG-SS+PRO-NH2} \rightarrow \text{mPEG-OC(O)—}CH_2CH_2\text{—CONH-PRO,}$$

the remaining ester linkage is subject to rapid hydrolysis and detachment of PEG from the modified protein. Too rapid a hydrolysis rate can preclude use of a PEG derivative for many applications. Several approaches have been adopted to solve the problem of hydrolytic instability. For example, mPEG succinimidyl carbonate has been proposed, which contains only ether linkages in the polymer backbone and reacts with proteins to form a conjugate that is not subject to hydrolysis.

In view of the above, it would be desirable to provide alternative PEG derivatives that are suitable for drug delivery systems, including delivery of proteins, enzymes, and small molecules, or for other biotechnology uses. It would also be desirable to provide alternative PEG derivatives that could enhance drug delivery systems or biotechnology products.

SUMMARY OF THE INVENTION

In one aspect, the present invention provides chemically active polyethylene glycols and related polymers that are suitable for coupling to other molecules. The polyethylene glycol derivatives provided herein, when covalently attached to another molecule, form water-soluble conjugates in which the linkage between the polymer and the bound molecule is subject to predetermined cleavage. This allows for controlled delivery of the bound molecule into its surrounding environment.

The polymers of the invention contain weak, hydrolytically unstable linkages near the reactive end of the polymer that provide for a sufficient circulation period for a drug-PEG conjugate, followed by hydrolytic breakdown of the conjugate and release of the bound molecule.

According to yet another aspect, also forming part of the present invention are (i) methods of preparing the degradable active PEGs described herein and related polymers, (ii) conjugates, and (iii) methods for preparing such PEG conjugates.

The PEG and related polymer derivatives of the invention are capable of imparting improved water solubility, increased size, a slower rate of kidney clearance, and reduced immunogenicity to a conjugate formed by covalent attachment thereto, while also providing for controllable hydrolytic release of the bound molecule into an aqueous environment—by virtue of the design of the linkages provided herein. The invention can be used to enhance the solubility and blood circulation lifetime of drugs in the bloodstream, while also delivering a drug into the bloodstream that, subsequent to hydrolysis, is substantially free of PEG. The invention is especially useful in those cases where drugs, when permanently conjugated to PEG, demonstrate reduced activity. By using a degradable PEG as provided herein, such drugs can maintain their therapeutic activity when in conjugated form, by virtue of the cleavable nature of the PEGs of the invention.

In general form, the polymer derivatives of the invention and their conjugates can be described by the following equations:

$$\text{POLY(-W-T)}_y\text{+Y-P'}\rightarrow\text{POLY(-W-X-P')}_y\text{+H}_2\text{O}\rightarrow$$

$$\rightarrow\text{POLY-G}_y\text{+(I-X-P')}$$

In the above equations,

"POLY" is a linear or branched polyethylene glycol of molecular weight from 300 to 100,000 daltons. POLY can also be a related non-peptidic polymer as described in greater detail below;

"y" is the number of chemically active groups on POLY and is the number of molecules that can be bound to POLY;

W is a hydrolytically unstable group;

T is a reactive group (i.e., is reactive with Y);

Y-P' represents a molecule for conjugation to POLY, where Y is a reactive group that is reactive with T, and P' is the portion of the molecule that is to be bound and released, including, for example, a peptide P' in which Y is an amine moiety and T is a PEG activating moiety reactive with an amine;

X is the new linkage formed by reaction of Y and T; and

G and I are new groups formed by hydrolysis of W.

Examples of hydrolytically unstable groups, W, include carboxylate esters, phosphate esters, acetals, imines, orthoesters, peptides and oligonucleotides. The variables, T and Y, are groups that react with each other. There are many examples of such groups known in organic chemistry. Some examples include the following combinations: active esters reacting with amines, isocyanates reacting with alcohols and amines, aldehydes reacting with amines, epoxides reacting with amines, and sulfonate esters reacting with amines, among others.

Examples of P' include peptides, oligonucleotides and other pharmaceuticals.

Examples of X, the linkage resulting from reaction of Y and T, include amide from reaction of active esters with amine, urethane from reaction of isocyanate with hydroxyl, and urea from reaction of amine with isocyanate.

Examples of G and I, the new groups formed upon hydrolysis of W, are alcohol and acid from hydrolysis of carboxylate esters, aldehyde and alcohol from hydrolysis of acetals, aldehyde and amine from hydrolysis of imines, phosphate and alcohol from hydrolysis of phosphate esters, amine and acid from hydrolysis of peptide, and phosphate and alcohol from hydrolysis of oligonucleotides.

An embodiment of the invention is shown in the following equation demonstrating conjugation of a hydrolyzable methoxy-PEG (mPEG) polymer derivative with a peptide drug, followed by hydrolytic release of the peptide. In the embodiment below, the weak linkage, W, contains a hydrolyzable ester group.

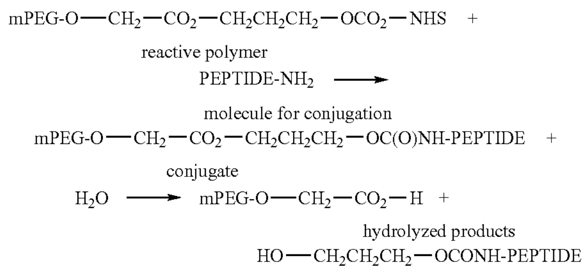

The released exemplary peptide contains no polymer, in this case, mPEG. Rather, the released peptide contains an additional short molecular fragment, which is sometimes called a "tag". This tag is the portion of the linkage opposite the PEG from the hydrolytically unstable linkage. In the above example, the tag portion is the '$HO—(CH_2)_3—O—C(O)—$' which remains attached to the released peptide.

Thus, the invention provides activated PEGs and other related polymers containing hydrolytically unstable linkages. The polymers are useful, when conjugated to a drug or other molecule, for controlled delivery of such molecule to its surrounding environment. Several types of linkages, including ester linkages, are suitable for use as the hydrolytically unstable linkage as provided herein. However, the ester linkages of the present polymers, in contrast to mPEG-SS and mPEG-SG, provide for variation and control of the rate of hydrolytic degradation.

The foregoing and other objects, advantages, and features of the invention, and the manner in which the same are accomplished, will be more readily apparent upon consideration of the following detailed description of the invention taken in conjunction with the accompanying drawings, which illustrate an exemplary embodiment of the invention.

DETAILED DESCRIPTION

Figure 1:
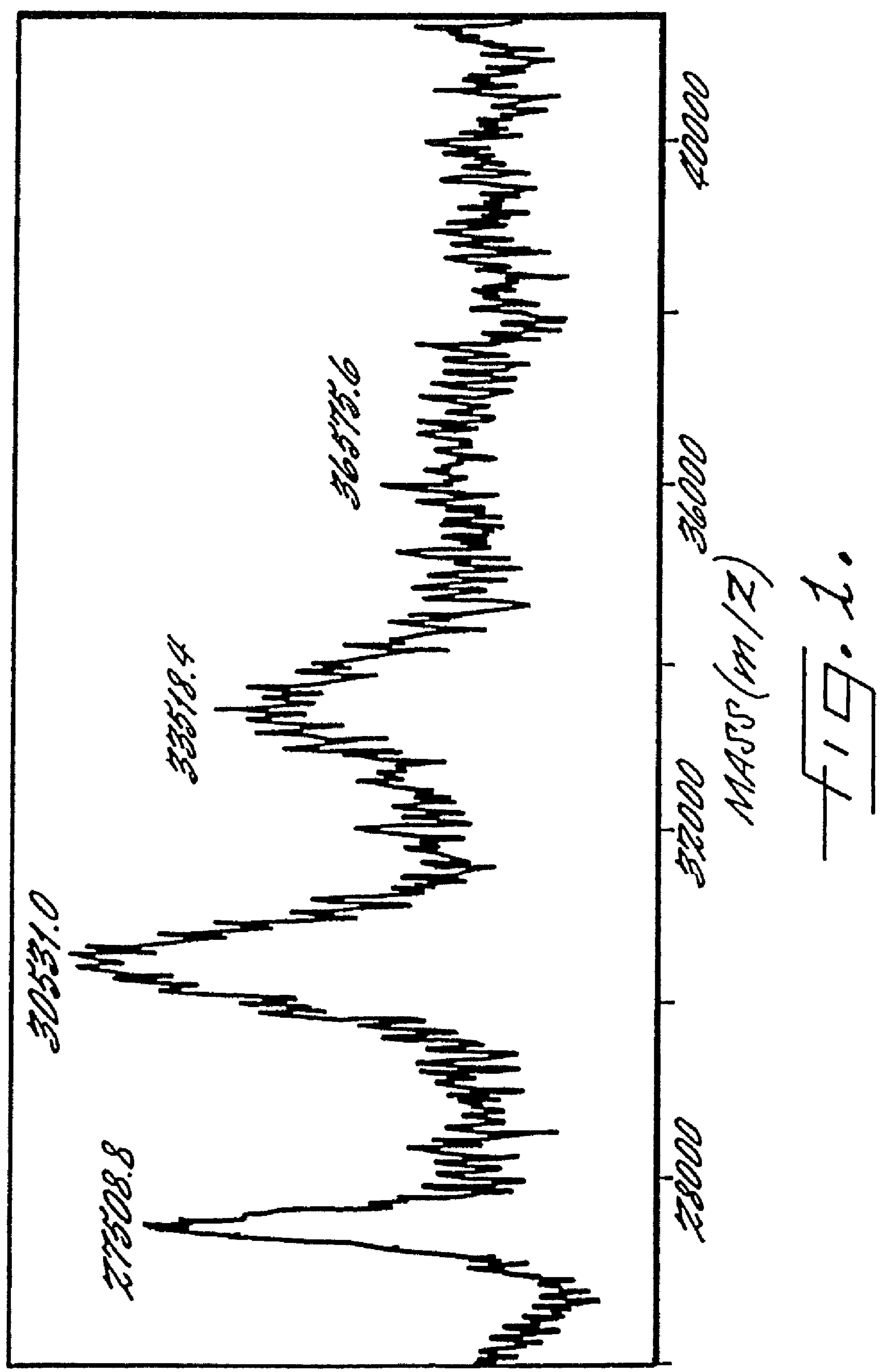
FIG. 1 is a MALDI-MS spectrum of the molecular weight distribution of an mPEG-HBA-subtilisin conjugate at 1 day after preparation as described in Example 8.

The following detailed description describes various embodiments of the invention as described by the following general equations presented in the preceding summary:

$$\text{Poly(-W-T)}_y\text{+Y-P'}\rightarrow\text{Poly(-W-X-P')}_y\text{+H}_2\text{O}\rightarrow$$

$$\text{Poly-G}_y\text{+I-X-P'}$$

The Polymer

In the discussion below, POLY will often be referred to for convenience as PEG or as poly(ethylene glycol). However, it is to be understood that other related polymers are also suitable for use in the practice of the invention in place of PEG and that the use of the term PEG or poly(ethylene glycol) is intended to be inclusive and not exclusive in this respect.

Poly(ethylene glycol) is preferred in the practice of the invention. PEG is used in biological applications because it has properties that are highly desirable and is generally approved for biological or biotechnological applications. PEG typically is clear, colorless, odorless, soluble in water, stable to heat, inert to many chemical agents, does not hydrolyze or deteriorate, and is non-toxic. Poly(ethylene glycol) is considered to be biocompatible, which is to say that PEG is capable of coexistence with living tissues or organisms without causing harm. More specifically, PEG is not immunogenic, which is to say that PEG does not tend to produce an immune response in the body. When attached to a moiety having some desirable function in the body, the PEG tends to mask the moiety and can reduce or eliminate an immune response so that an organism can tolerate the presence of the moiety, in PEGylated form. Accordingly, the activated PEGs of the invention should be substantially non-toxic and not tend to substantially produce an immune response or cause clotting or other undesirable effects.

Water-soluble polymers other than PEG are suitable for similar modification in accordance with the invention described herein. These other polymers include poly(vinyl alcohol) ("PVA"); other poly(alkylene oxides) such as poly (propylene glycol) ("PPG") and the like; and poly(oxyethylated polyols) such as poly(oxyethylated glycerol), poly(oxyethylated sorbitol), and poly(oxyethylated glucose), and the like. The polymers can be homopolymers or random or block copolymers and terpolymers based on monomers of the above polymers, straight chain or branched, substituted or unsubstituted, e.g., similar to mPEG and other capped, mono-functional PEGs having a single active site available for attachment to a linker.

Specific examples of such suitable polymers include poly (oxazoline), poly(acryloylmorpholine) ("PAcM"), and poly (vinylpyrrolidone)("PVP"). PVP and poly(oxazoline) are well-known polymers in the art and their preparation and use in the syntheses described herein for embodiments based upon mPEG should be readily apparent to the skilled artisan. PAcM and its synthesis and use are described in U.S. Pat. Nos. 5,629,384 and 5,631,322, the contents of which are incorporated herein by reference in their entireties.

Definitions

It should be understood that by "drug" is meant any substance intended for the diagnosis, cure, mitigation, treatment, or prevention of disease in humans and other animals, or used to otherwise enhance physical or mental well-being. The invention is useful, for example, for delivery of biologically active substances that generally have some activity or function in a living organism or in a substance taken from a living organism.

The terms "group," "functional group," "moiety," "active moiety," "reactive site," and "radical" are all somewhat synonymous in the chemical arts and are used in the art and herein to refer to distinct, definable portions or units of a molecule and to units that perform some function or activity and are reactive with other molecules or portions of molecules.

The term "linkage" is used herein to refer to groups that are normally formed as the result of a chemical reaction. Herein, such linkages are typically covalent linkages.

"Hydrolytically stable linkage" means a linkage that is stable in water and does not react with water under useful or normal conditions of pH for an extended period of time, potentially indefinitely.

"Hydrolytically unstable linkage" is a linkage or functionality that reacts with water, typically causing a molecule to separate (or cleave) into two or more components. Such a linkage is said to be "subject to hydrolysis" and to be "hydrolysable". The time it takes for the linkage to react with water is referred to as the rate of hydrolysis and is usually measured in terms of its half-life.

The Hydrolytically Unstable Linkage (W) and Reactive Groups, T and Y

In a particular embodiment, the invention includes poly (ethylene glycols) containing, for example, an ester group as the weak linkage and a succinimidyl ester as the reactive group useful for coupling to amine-containing molecules. The resulting conjugates can be delivered in vivo or into a substance taken from a living entity. Exemplary polymers, and in particular, linkages, are provided below.

$$\text{PEG-W—CO}_2\text{—NHS}$$

where W=—$O_2C$—$(CH_2)_b$—O— b=1-5
—O—$(CH_2)_bCO_2$—$(CH_2)_c$— b=1-5, c=2-5
—O—$(CH_2)_b$—$CO_2$—$(CH_2)_c$—O— b=1-5, c=2-5

The invention also encompasses poly(ethylene glycols) containing an ester group as the weak linkage and an isocyanate as the reactive group useful for coupling to amine- and alcohol-containing molecules, as exemplified below.

$$\text{PEG-W—N═C═O}$$

where W=—O—$(CH_2)_b$—$CO_2$—$(CH_2)_c$— b=1 to 5, c=2 to 5

As a further example, the invention also includes poly (ethylene glycols) containing an acetal as the weak linkage and a succinimidyl ester as the reactive group useful, for example, for coupling to an amine-containing molecule.

$$\text{PEG-W—CO}_2\text{—NHS,}$$

where, for example, W equals:

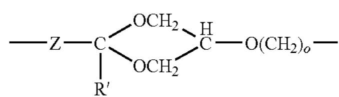

-continued

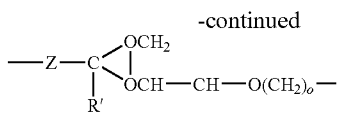

In the above illustrative structures,
o=1-10,
Z=—O—$C_6H_4$— and —O—$(CH_2)_d$—$CH_2$— d=1-5
R'=alkyl or H.

In yet another embodiment, the invention encompasses poly(ethylene glycols) containing an imine group as the weak linkage and a succinimidyl ester as the reactive group, e.g., useful for coupling to, for example, an amine-containing molecule.

PEG-W—$CO_2$—NHS where W=—Z—CH═N—$(CH_2)_b$—O— b=1-5
Z=—O—$C_6H_4$—
—O—$(CH_2)_b$—$CH_2$— b=1-5

According to yet another embodiment, the invention also includes poly(ethylene glycols) containing a phosphate ester group as the weak linkage and a succinimidyl ester as the reactive group, e.g., useful for coupling to an amine-containing molecule.

PEG-W—$CO_2$—NHS where W=—$(CH_2)_b$—$OPO_3$—$(CH_2)_{b'}$— b and b'=1-5

According to yet another exemplary embodiment, the invention includes poly(ethylene glycols) containing an ester-linked amino acid as the weak linkage and a succinimidyl ester as the reactive group, e.g., useful for coupling to an amine-containing molecule. An advantage of this derivative is that its hydrolytic breakdown results in a biologically acceptable amino acid attached to the released molecule:

PEG-W—$CO_2$—NHS where W=—O—$(CH_2)_b$—$CO_2$—$(CH_2)_{b'}$—CH(NH-t-Boc)-
b=1-5,
b'=1-5, and
t-Boc=$(CH_3)_3$C—O—CO—.

In yet a further embodiment, the invention includes poly (ethylene glycols) containing a peptide as the weak linkage and a succinimidyl ester as the reactive group useful for coupling to an amine-containing molecule. An advantage of this particular type of derivative is that its hydrolytic breakdown typically results in a biologically acceptable peptide fragment attached to the released molecule:

PEG-W—$CO_2$—NHS where W=—C(O)(NH—CHR—CO)$_a$—NH—CHR—
a=2-20
R=the set of substituents typically found on α-amino acids In yet another exemplary embodiment, the invention includes poly(ethylene glycols) containing an oligonucleotide forming the weak linkage and a succinimidyl ester as the reactive group, e.g., useful for coupling to an amine-containing molecule. An advantage of this particular type of derivative is that its hydrolytic breakdown results in a biologically acceptable oligonucleotide fragment attached to the released molecule:

PEG-W—$CO_2$—NHS where W=oligonucleotide.

As previously described, polymers for use in the invention can be straight chain or branched. That is to say, branched activated PEGs can be prepared in accordance with the invention where such PEGs possess weak linkages near the reactive end of the polymer for controlled hydrolytic degradation. Illustrative branched PEGs are described in International Publication No. WO 96/21469, entitled, "Multi-Armed, Monofunctional, and Hydrolytically Stable Derivatives of Poly(Ethylene Glycol) and Related Polymers For Modification of Surfaces and Molecules", filed Jan. 11, 1996, the content of which is incorporated herein by reference in its entirety. Branched PEGs such as these can then be modified in accordance with the present teachings.

The invention is illustrated with respect to several particular examples below, including determination of hydrolysis half-lives for representative hydrolyzable polymer derivatives and conjugates.

EXAMPLES

Example 1

PREPARATION OF

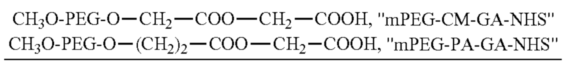

Reactions ($n$ = 1 or 2):

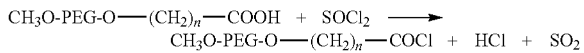

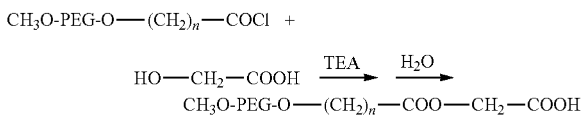

$CH_3O$-$PEG_{3000}$-O—$(CH_2)_{1,2}$—COOH (3.0 g, 1 mmol, mPEG-CM or mPEG-PA) was azeotropically dried with 60 ml of toluene under $N_2$. After two hours, the solution was cooled to room temperature, followed by injection of a solution of thionyl chloride (2 ml, 4 mmol) in $CH_2Cl_2$. The resulting solution was stirred at room temperature overnight. The solvent was condensed on a rotary evaporator and the residual syrup was dried in vacuo for about four hours over $P_2O_5$ powder.

Glycolic acid (0.2 g, 2.7 mmole) was azeotropically distilled with 70 ml of 1,4-dioxane and the distillation was stopped when approximately 20 ml of solution remained. The solution was slowly cooled to room temperature under $N_2$. The glycolic acid/dioxane solution was then added to the dried PEG acyl chloride. After the PEG was dissolved, 0.6 ml of dry triethylamine was injected to the system (precipitate formed immediately) and the solution was stirred overnight. The salt was removed by filtration and the filtrate was condensed on a rotary evaporator at 55° C. and dried in vacuo. The crude product was then dissolved in 100 ml of distilled water and the pH of the solution was adjusted to 3.0. The aqueous phase was extracted three times with a total of 80 ml of methylene chloride. The combined organic phase was dried over sodium sulfate, filtered to remove salt, condensed on a rotary evaporator, and added to 100 ml of ethyl ether. The precipitate was collected by filtration and dried in vacuo.

Yield 2.55 g (85%). $^1H$ NMR (DMSO-$d_6$): δ 3.5 (br m, PEG), 4.3-4.6 (s, PEGOCH$_2$COOCH$_2$COOH), 2.59 (t, PEGOCH$_2$CH$_2$COO(PA)), 4.19 (s, PEGOCH$_2$COO(CM)).

Example 2

PREPARATION OF
HOOC—CH$_2$—OOC—CH$_2$—O-PEG-O—CH$_2$—COO—CH$_2$—COOH

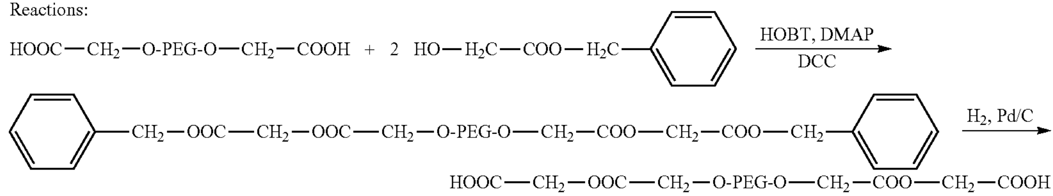

Difunctional carboxymethyl $PEG_{20,000}$-ester benzyl glycolate: Difunctional carboxymethyl PEG 20,000 (4 gram, 0.4 mmol acid group), benzyl glycolate (0.6 mmol), dimethylaminopyridine (0.44 mmol), 1-hydroxybenzotriazole (0.4 mmol) and dicyclohexylcarbodiimide (0.56 mmol) were dissolved in 40 ml of methylene chloride. The solution was stirred at room temperature under $N_2$ overnight. The solvent was then removed under vacuum and the resulting residue was added to 20 ml of toluene at 40° C. The undissolved solid was removed by filtration and the filtrate was added to 200 ml of ethyl ether. The precipitate was collected by filtration and dried in vacuo.

Yield: 4 gram (100%). $^1$H NMR (DMSO-$d_6$): δ 3.5 (br m, PEG), 4.81 (s, PEGOCH$_2$COOCH$_2$COOCH$_2$C$_6$H$_5$), 5.18 (s, PEGOCH$_2$COOCH$_2$COOCH$_2$C$_6$H$_5$), 7.37 (s, PEGOCH$_2$COOCH$_2$COOCH$_2$C$_6$H$_5$), 4.24 (s, PEGOCH$_2$COOCH$_2$COOCH$_2$C$_6$H$_5$).

Difunctional carboxymethyl PEG-ester benzyl glycolate 20,000 (3 gram) and Pd/C (10%, 0.8 gram) were added to 30 ml of 1,4-dioxane. The mixture was shaken with $H_2$ (40 psi) at room temperature overnight. The Pd/C was removed by filtration and the solvent was condensed by rotary evaporation. The resulting syrup was added to 100 ml of ether. The precipitated product was collected by filtration and dried in vacuo.

Yield 2.4 gram (80%). $^1$H NMR (DMSO-$d_6$): δ 3.5 (br m, PEG), 4.56 (s, PEGOCH$_2$COOCH$_2$COOH), 4.20 (s, PEGOCH$_2$COOCH$_2$COOH).

Example 3

PREPARATION OF
CH$_3$O-PEG-O—(CH$_2$)$_{1,2}$—COO—CH$_2$—COONHS

Reactions ($n$ = 1 or 2):

CH$_3$O-PEG-O—(CH$_2$)$_n$—COO—CH$_2$—COOH +

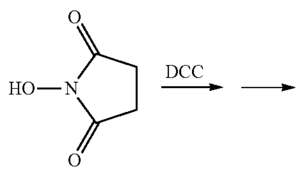

-continued

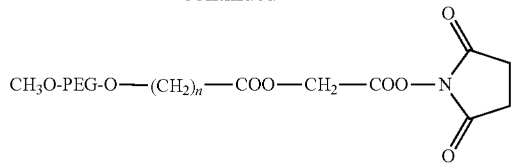

CH$_3$O-PEG-O—(CH$_2$)$_{1,2}$—COO—CH$_2$—COOH (1 g, approx. 0.33 mmol) and 42 mg N-hydroxysuccinimide (NHS) (0.35 mmol) was dissolved in 30 ml of dry methylene chloride. To this was added dicyclohexylcarbodiimide (DCC) (80 mg, 0.38 mmol) in 5 ml of dry methylene chloride. The solution was stirred under nitrogen overnight and the solvent was removed by rotary evaporation. The resulting syrup was re-dissolved in 10 ml of dry toluene and the insoluble solid was filtered off. The solution was then precipitated into 100 ml of dry ethyl ether. The precipitate was collected by filtration and dried in vacuo.

Yield 0.95 g (95%). $^1$H NMR (DMSO-$d_6$): δ 3.5 (br m, PEG), 5.15-5.21 (s, PEGOCH$_2$COOCH$_2$COONHS), 2.67 (t, PEGOCH$_2$CH$_2$COO(PA)), 4.27 (s, PEGOCH$_2$COO ppm (CM)), 2.82 (s, NHS, 4H).

Example 4

PREPARATION OF

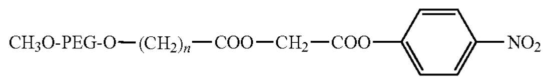

Reactions ($n$ = 1 or 2):

CH$_3$O-PEG-O—(CH$_2$)$_n$—COO—CH$_2$—COOH +

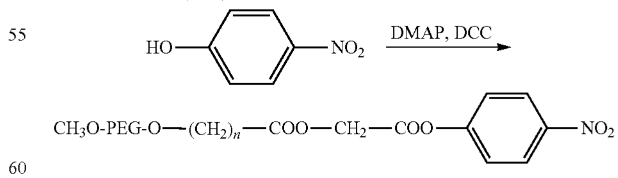

CH$_3$O-PEG-O—(CH$_2$)$_{1,2}$—COO—CH$_2$—COOH (1.5 g, approx. 0.5 mmol), 140 mg p-nitrophenol (1 mmol) and 65 mg dimethylaminopyridine (DMAP) (0.525 mmol) were dissolved in 30 ml of dry methylene chloride. To the resulting solution was added dicyclohexylcarbodiimide (DCC) (120 mg, 0.575 mmole) in 5 ml of dry methylene chloride. The solution was stirred under nitrogen overnight and the solvent was removed by rotary evaporation. The resulting syrup was redissolved in 10 ml of dry toluene and the insoluble solid was removed by filtration. Then the solution was precipitated into 100 ml of dry ethyl ether. The product was reprecipitated with ethyl ether, then collected by filtration and dried in vacuo.

Yield 1.425 g (95%). $^{1}$H NMR (DMSO-$d_6$): δ 3.5 (br m, PEG), 5.01 (s, PEGOCH$_2$COOC$\underline{H}_2$COONP), 2.69 (t, PEGOC$\underline{H}_2$CH$_2$COO(PA)), 8.35 & 7.$\underline{48}$ (d&d, $H_a$ & $H_b$ in NP, 4H).

Example 5

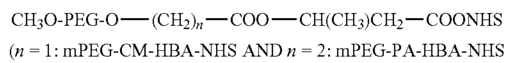

PREPARATION OF CH$_3$O-PEG-O—(CH$_2$)$_n$—COO—CH(CH$_3$)CH$_2$—COONHS ($n$ = 1: mPEG-CM-HBA-NHS AND $n$ = 2: mPEG-PA-HBA-NHS

Reactions ($n$ = 1 or 2):

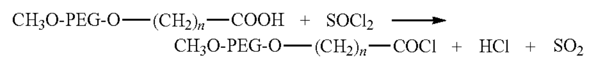

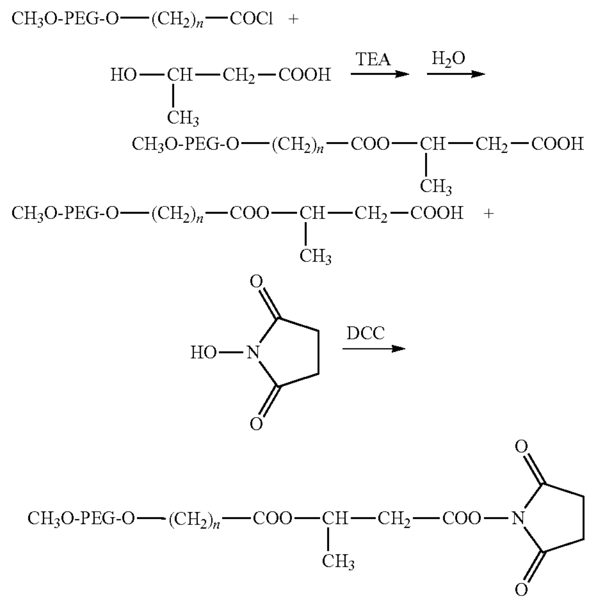

CH$_3$O-PEG-O—(CH$_2$)$_n$—COOH 3000 (3.0 g, 1 mmol) was azeotropically dried with 60 ml of toluene under N$_2$. After two hours, the solution was slowly cooled to room temperature. To the resulting solution was added thionyl chloride solution (3 ml, 6 mmol) in CH$_2$Cl$_2$, and the solution was stirred overnight. The solvent was condensed by rotary evaporation and the syrup was dried in vacuo for about four hours over P$_2$O$_5$ powder. 3-hydroxybutyric acid (HBA, 0.30 g, 2.7 mmol) was azeotropically dried with 70 ml of 1,4-dioxane on a rotary evaporator. The distillation was stopped when approximately 20 ml of solution remained. This solution was then slowly cooled to room temperature under N$_2$, and the solution was added to the dried PEG acyl chloride. After the PEG was dissolved, 0.6 ml of dry triethylamine was injected to the system (precipitate formed immediately) and the solution was stirred overnight. The salt was removed by filtration and the filtrate was condensed on a rotary evaporator at 55° C. and dried in vacuo. The crude product was then dissolved in 100 ml of distilled water and the pH of the solution was adjusted to 3.0. The aqueous phase was extracted three times with a total of 80 ml of methylene chloride. The organic phase was dried over sodium sulfate, filtered to remove salt, condensed on a rotary evaporator, and added to 100 ml of ethyl ether. The precipitate was collected by filtration and dried in vacuo. Yield 2.76 g (92%). $^{1}$H NMR (DMSO-$d_6$): δ 3.5 (br m, PEG), 2.54 (d, PEGOCH$_2$COOCH(CH$_3$)CH$_2$COOH), 5.1 (h, PEGOCH$_2$COOCH(CH$_3$)CH$_2$CO$\underline{O}$H), 1.2 (d, PEG-OCH$_2$COOCH(C$\underline{H}_3$)CH$_2$COOH), 2.54 (t, PEGOCH$_2$C$\underline{H}_2$COO(PA)), 4.0$\underline{55}$ (s, PEGOC$\underline{H}_2$COO(CM)).

mPEG-ester butyric acid NHS ester (CM-HBA-NHS or PA-HBA-NHS): mPEG$_{3000}$-ester butyric acid (1 g, approx., 0.33 mmol, CM-HBA-COOH or PA-HBA-COOH) and 42 mg N-hydroxysuccinimide (NHS) (0.35 mmol) were dissolved in 30 ml of dry methylene chloride. To this solution was added dicyclohexylcarbodiimide (DCC) (80 mg, 0.38 mmole) in 5 ml of dry methylene chloride. The solution was stirred under nitrogen overnight and the solvent removed by rotary evaporation. The residual syrup was re-dissolved in 10 ml of dry toluene and the insoluble solid was removed by filtration. The solution was then precipitated into 100 ml of dry ethyl ether. The precipitate was collected by filtration and dried in vacuo.

Yield 0.94 g (94%). $^{1}$H NMR (DMSO-$d_6$): δ 3.5 (br m, PEG), 3.0-3.2 (m, COOCH(CH$_3$)C$\underline{H}_2$COONHS), 5.26 (h, COOCH(CH$_3$)CH$_2$—COONHS), $\overline{1}$.3 (d, COOCH(CH$_3$)C$\underline{H}_2$COONHS), 2.54 (t, OCH$_2$C$\underline{H}_2$COO(PA)), 4.1 (s, OC$\underline{H}_2$COO(CM)), 2.81 (s, NHS).

Example 6

Determination of the Hydrolytic Half-Lives of the Ester Linkages Contained in Four Exemplary PEG-PEG Conjugates Reactions ($n$ = 1 or 2):

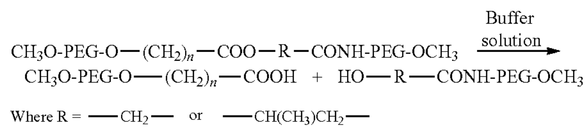

A. Preparation of CH$_3$O-PEG-O—(CH$_2$)$_n$—COO—CH$_2$—CONH-PEG-OCH$_3$ (PEG-PEG conjugates): CH$_3$O-PEG$_{3000}$-O—(CH$_2$)$_n$—COO—CH$_2$—COOH (0.5 g), 1 equiv. of mPEG$_{2000}$-NH$_2$ and 1 equiv. of 1-hydroxybenzotriazole (HOBT) were dissolved in 50 ml of methylene chloride. To this solution was added one equivalent of dicyclohexylcarbodiimide (DCC) and the solution was stirred at room temperature overnight. The solvent was partially evaporated, the insoluble salt was filtered, and the filtrate was added into a large excess of ethyl ether. The precipitate was collected by filtration and dried in vacuo. Yield: 0.8 g (95%). $^{1}$H MNR (DMSO-$d_6$): δ 3.5 (br m, PEG), 2.34 (t, —CONHC$\underline{H}_2$CH$_2$O-PEG-).

B. Determination of hydrolytic half-lives of PEG ester conjugates formed by reaction of CM-GA, PA-GA, CM-HBA or PA-HBA with a PEG amine: The conjugates from A. above and 20 wt % PEG 20,000 (as an internal standard) were dissolved in a buffer solution. The concentrations of each of the conjugates (C) and their hydrolysis products were monitored by HPLC-GPC (Ultrahydrogel 250 column, 7.8×300 mm, Waters) at predetermined times. The hydrolytic half-lives were obtained from the slope of the natural logarithm of C at the time, t, minus C at infinite time versus time assuming $1^{st}$ order kinetics.

TABLE 1

HYDROLYSIS HALF-LIVES (DAYS, UNLESS NOTED OTHERWISE) OF THE ESTER LINKAGES CONTAINED IN THE ABOVE CONJUGATES. (±10%)

| | Double-Ester PEG Used to Form Conjugate | | | | | | |
|---|---|---|---|---|---|---|---|
| | CM-GA | PA-GA | | CM-HBA | | PA-HBA | |
| pH | 7.0 | 7.0 | 8.1 | 7.0 | 8.1 | 7.0 | 8.1 |
| 23° C. | 3.2 | 43 | 6.5 | — | 15 | — | 120 |
| 37° C. | 14 h | 7.6 | — | 14 | — | 112 | — |
| 50° C. | 4 h | 2.2 | — | 5 | — | 58 | — |

Example 7

Determination of Hydrolysis Half-Lives of the Ester Linkages Contained in Four Exemplary PEG Reagents

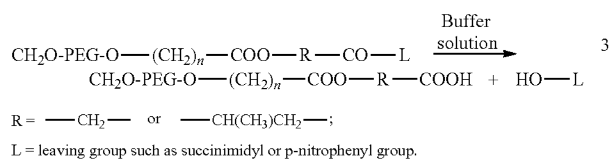

Determination of hydrolysis half-lives of PEG active esters: Measurements were conducted using a HP8452a UV-VIS spectrophotometer. In an experiment, 1 mg of a given PEG active ester was dissolved in 3.0 ml of buffer solution and shaken promptly to obtain dissolution as soon as possible. The solution was then transferred into a UV cuvette and the absorbance at 260 nm (for NHS ester) or at 402 nm (for the p-nitrophenyl ester) was followed as a function of time. The hydrolytic half-life was determined from the first order kinetic plot (natural logarithm of final absorbance minus absorbance at the time t versus time).

TABLE 2

HYDROLYSIS HALF-LIVES OF SUCCINIMIDYL ACTIVE ESTERS (R = NHS) AND P-NITROPHENYL ACTIVE ESTERS (R = NP) OF PEG-ESTER ACIDS AT PH 8.1 AND ROOM TEMPERATURE

| R | CM-GA-R | PA-GA-R | CM-HBA-R | PA-HBA-R |
|---|---|---|---|---|
| NHS | 11 s | 11 s | 12 min | 12 min |
| NP | 7 min | 7 min | — | — |

Example 8

Hydrolytic Release of PEG from a PEG-Protein Conjugate by MALDI-TOF Mass Spectrometry Modification of subtilisin with an illustrative PEG derivative: To a subtilisin solution (1 ml, 2 mg/ml in 0.2M boric buffer, pH 8.0) was added 15 mg $mPEG_{3000}$-CM-HBA-NHS. The solution was placed in an automatic shaker at room temperature. At predetermined time periods, 50 µl of the solution was removed and preserved in a refrigerator for MALDI-TOF MS measurement.

MALDI Analyses: MALDI spectra were measured on a PerSeptive Biosystems' Voyager linear time-of-flight (TOF) instrument. Briefly, a nitrogen laser lamda=337 nm, 10 ns pulse width) was used to generate ions which were extracted with a potential of 30 kV. Ions drifted through a 1.3 m drift tube and were monitored in positive ion mode.

Protein samples were dissolved in deionized $H_2O$ or 50 mM NaCl solution to a concentration of approximately 10 pmol/µl. The matrix, 3,5-dimethoxy-4-hydroxycinnamic acid (sinapinic acid), was dissolved in an 80:20 by volume ratio of acetonitrile to deionized water at a concentration of 10 mg/ml. 1 µl of the solution was deposited on the sample plate and then mixed with 1 µl of matrix solution. The sample was allowed to crystallize by solvent evaporation under ambient conditions.

Figure 2:
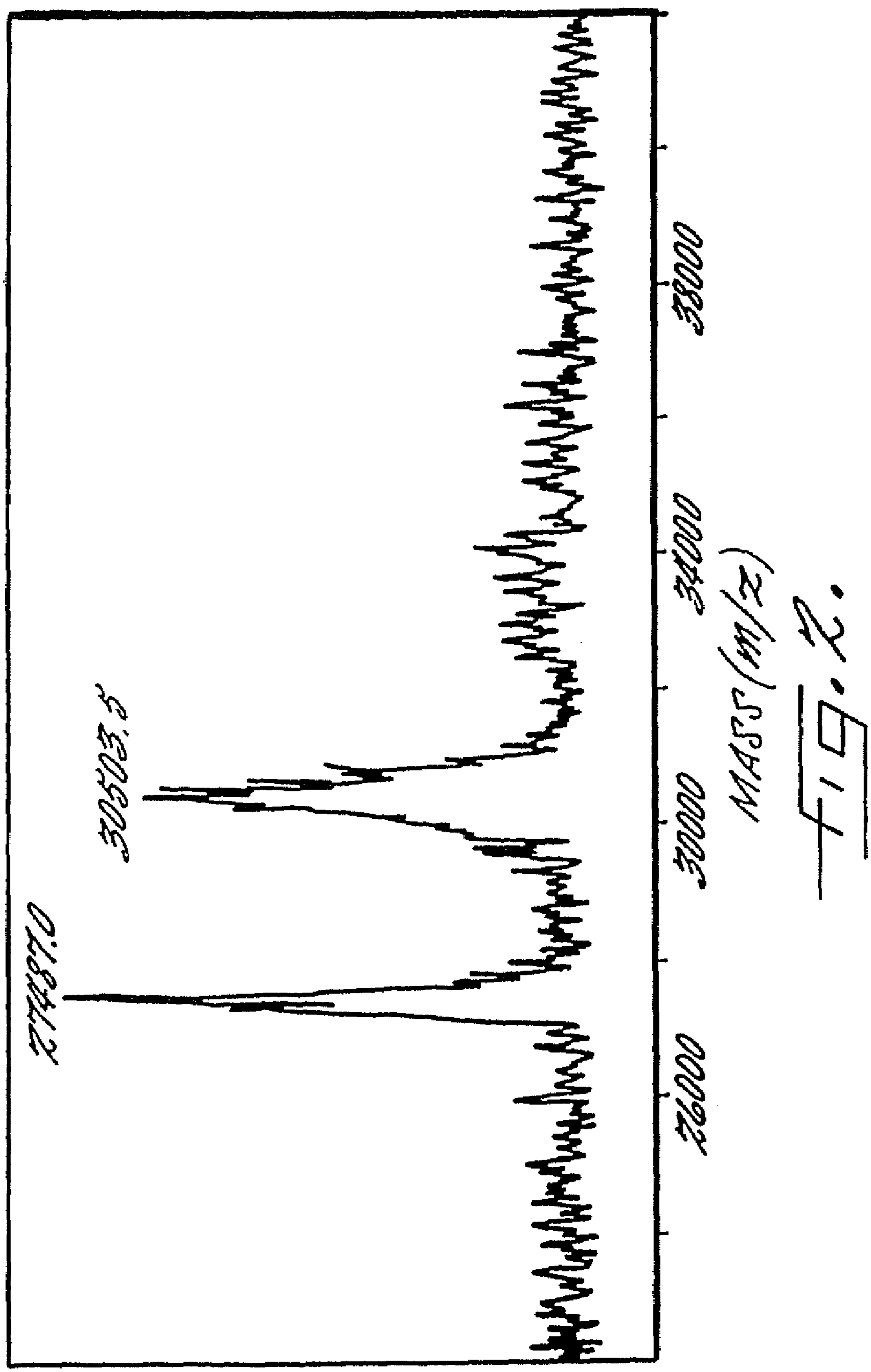
FIG. 2 is a MALDI-MS spectrum of the molecular weight distribution of an mPEG-HBA-subtilisin conjugate at 8 days after preparation as described in Example 8.
Figure 3:
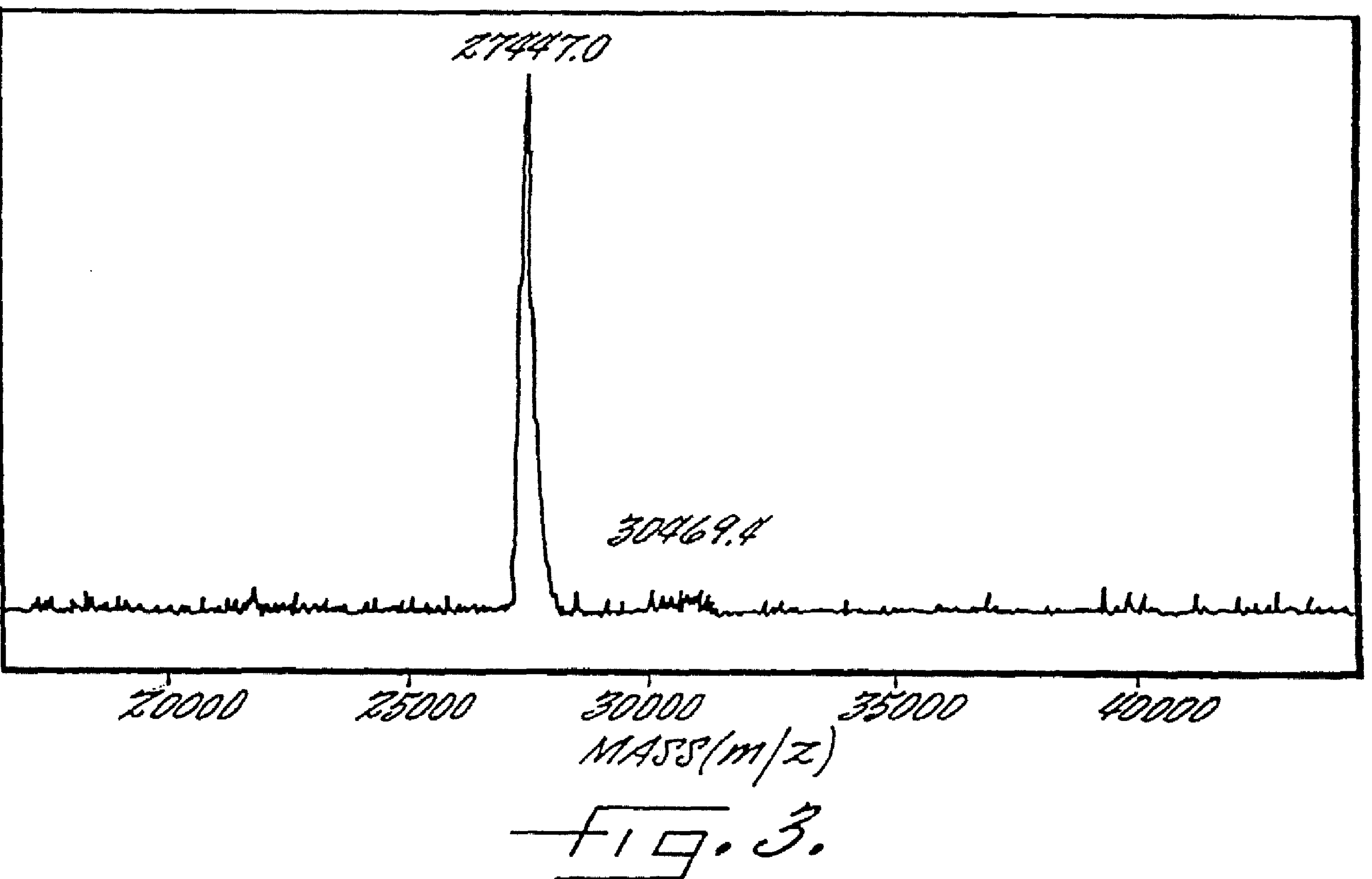
FIG. 3 is a MALDI-MS spectrum of the molecular weight distribution of an mPEG-HBA-subtilisin conjugate at 14 days after preparation as described in Example 8.

MALDI-MS spectra of the molecular weight distribution of mPEG-HBA and its subtilisin conjugate are shown in FIGS. 1 through 3. Each of the figures represents the solution at a different time subsequent to preparation. FIG. 1 is at 1 day. FIG. 2 is at 8 days. FIG. 3 is at 14 days.

Example 9

PREPARATION OF

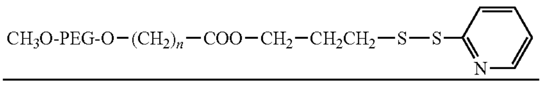

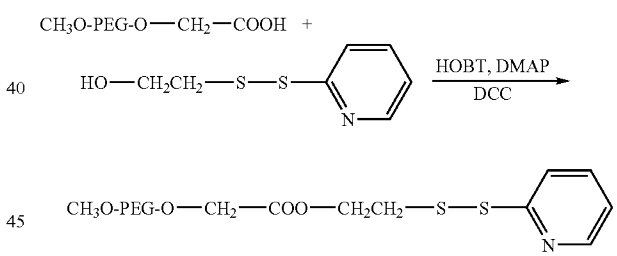

$CH_3O$-PEG-O—$CH_2$—COOH 5000 (3.0 g, 0.6 mmol), 2-(2-pyridyldithio)ethanol (342 mg, 1.5 mmol), DMAP (180 mg, 1.44 mmol) and HOBT (93 mg, 0.61 mmol) were dissolved in 60 ml of dichloromethane. To this solution was added DCC (138 mg, 0.66 mmol) in 5 ml of dichloromethane. The solution was stirred at room temperature under $N_2$ overnight. The solvent was removed by rotary evaporation and 15 ml of toluene was added to the residue. After all PEG was dissolved, the solution was filtered to remove dicyclohexyl urea. To the solution was added 45 ml of methylene chloride and the solution was washed with sodium acetate buffer (0.1M, pH 5.0) containing 10% sodium chloride. The organic phase was dried over anhydrous sodium sulfate, filtered to remove salt, condensed on a rotary evaporator, and precipitated into 100 ml of ethyl ether. The product was collected by filtration and dried in vacuo. Yield 2.85 g (95%). $^1H$ NMR (DMSO-$d_6$): δ 3.5 (br m, PEG), 4.11 (s, PEGO$\underline{CH_2}$COO—), 4.30 (t, $COOCH_2CH_2SS$—) 7.29 (t, one aromatic proton), 7.77 (t+d, two aromatic protons), 8.46 (d, one aromatic proton).

Example 10

Determination of the Hydrolysis Half-Life of an Ester Linkage in an Illustrative PEG Derivative Reactions:

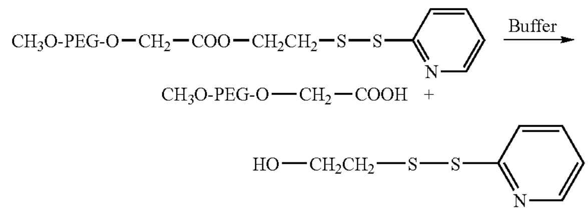

mPEG-CM-SSP and 20% PEG 20,000 (wt) (as internal standard) were dissolved in 10 mM phosphate buffer (pH 7.2) and a series of ampoules were sealed with each containing about 0.25 ml of above solution. The ampoules were stored as two groups, with one group at room temperature and the other at 37° C. For each measurement, one ampoule in each group was opened and the solution was analyzed. The concentrations of mPEG-CM-SSP and its hydrolysis product were determined by HPLC-GPC (Ultrahydrogel 250 column, Waters; 5 mM phosphate buffer pH 7.2 as mobile phase). The hydrolytic half-life was obtained from the slope of the natural logarithm of C at the time t minus C at infinite time versus time, assuming 1st order kinetics.

TABLE 3

HYDROLYTIC HALF-LIVES (DAYS) OF THE ESTER IN MPEG-CM-SSP. (10%)

| | pH 5.5 | pH 7.0 |
|---|---|---|
| Room temperature | 107 | 18 |
| 37° C. | 20 | 2.9 |

Example 11

PREPARATION OF $CH_2O$-PEG-O$(CH_2)_n$—$CO_2$-PEG-OCOONHS

Reactions ($n$ = 1 or 2):

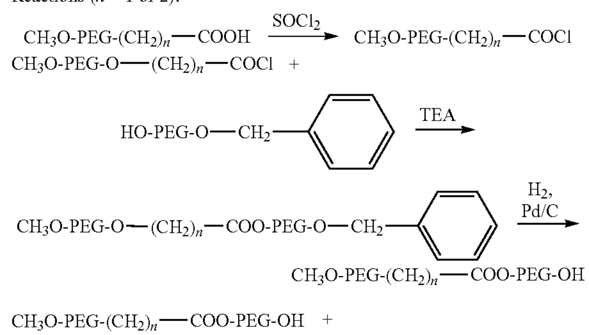

-continued

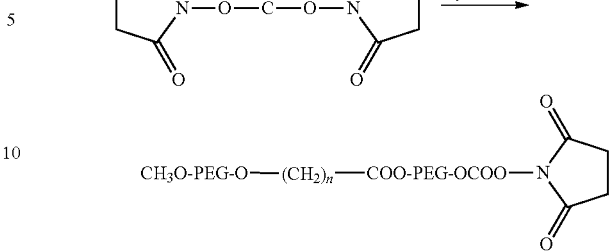

(a) Preparation of $CH_3O$-PEG-$OCH_2CH_2CO_2$-PEG-OBz

In a 100 ml round-bottom flask, a solution of $CH_3O$-PEG-O—$(CH_2)_n$—$CO_2H$ (MW=2000, 2 g, 1 mmol) was dissolved in toluene and azeotropically dried for two hours. After slowly cooling to room temperature, the solution was added to thionyl chloride (3 ml, 6 mmole) in methylene chloride and then stirred under $N_2$ overnight. The solvent was then removed by rotary evaporation and the residual syrup was dried in vacuo for about four hours over $P_2O_5$ powder. To the solid was added 5 ml of anhydrous methylene chloride and a solution (20 ml) of azeotropically dried BzO-PEG-OH (MW=3400, 2.04 g, 0.60 mmol) in toluene. To the resulting solution was added 0.6 ml of freshly distilled triethylamine and the solution was stirred overnight. The triethylamine salt was removed by filtration and the crude product was precipitated with ethyl ether and collected by filtration. The mixture was then purified by ion-exchange chromatography (DEAE sepharose fast flow column, Pharmacia). Pure $CH_3O$-PEG-O—$(CH_2)_n$—$CO_2$-PEG-OBz was obtained. Yield: 2.6 g (80%). NMR (DMSO-$d_6$): δ 3.5 (br m, PEG), 2.55 (t, —$OCH_2CH_2COOPEG$-), 4.14 (s, -$PEGOCH_2COOPEG$-), 4.13 (t, -$PEGOCH_2CH_2$—$COOCH_2CH_2OPEG$-), 4.18 (t, -$PEGOCH_2$—$COOCH_2CH_2OPEG$), 4.49 (s, -PEG-O—$CH_2$—$C_6H_5$), 7.33 (s+com, -PEG-O—$CH_2$—$C_6H_5$).

(b) Preparation of $CH_3O$-PEG-O—$(CH_2)_n$—$CO_2$-PEG-OH

A solution of 2 g of $CH_3O$-PEG-O—$(CH_2)_n$—$CO_2$-PEG-OBz in 1,4-dioxane was hydrogenolyzed with $H_2$ (2 atm) on 1 gram Pd/C (10%) overnight. The catalyst was removed by filtration, the solvent was condensed under vacuum and the solution was added to ethyl ether. The product was collected by filtration and dried under vacuum at room temperature to yield: 1.5 g (75%) of $CH_3O$-PEG-O—$(CH_2)_n$—$CO_2$-PEG-OH. NMR (DMSO-$d_6$): δ 3.5 (br m, PEG), 2.55 (t, —$OCH_2CH_2COOPEG$-), 4.14 (s, -PEG-$OCH_2COOPEG$-), 4.13 (t, -$PEGOCH_2CH_2COOCH_2CH_2OPEG$-), 4.18 (t, -$PEGOCH_2$—$COOCH_2CH_2OPEG$).

(c) Preparation of $CH_3O$-PEG-O—$(CH_2)_n$—$CO_2$-PEG-OCOONHS $CH_3O$-PEG-O—$(CH_2)_n$—$CO_2$-PEG-OH 5400 (1.25 g, 0.23 mmole) was azeotropically distilled with 100 ml acetronitrile and then cooled to room temperature. To this mixture was added disuccinimidyl carbonate (245 milligram, 0.92 mmole) and 0.1 ml of pyridine, and the solution was stirred at room temperature overnight. The solvent was then removed under vacuum, and the resulting solid was dissolved in 35 ml of dry methylene chloride. The insoluble solid was removed by filtration, and the filtrate was washed with pH 4.5 sodium chloride saturated acetate buffer. The organic phase was dried over anhydrous sodium sulfate, filtered, condensed by rotary evaporation, and precipitated into ethyl ether. The product was collected by filtration and dried in vacuo.

Yield: 1.20 g (96%), 100% substitution of succimidyl carbonate and no reagent left. NMR (DMSO-$d_6$): δ 3.5 (br m, PEG), 2.55 (t, —$OCH_2CH_2COOPEG$-), 4.14 (s, -PEG-$OCH_2COOPEG$-), 4.13 (t, -PEG$OCH_2CH_2COOCH_2CH_2OPEG$-), 4.18 (t, -PEG$OCH_2$—$COOCH_2CH_2OPEG$), 4.45 (t, -PEGO-$CH_2CH_2OCONHS$), 2.81 (s, NHS).

The invention has been described in particular exemplified embodiments. However, the foregoing description is not intended to limit the invention to the exemplified embodiments, and the skilled artisan should recognize that variations can be made within the scope and spirit of the invention as described in the foregoing specification. On the contrary, the invention includes all alternatives, modifications, and equivalents that may be included within the true spirit and scope of the invention as defined by the appended claims.

What is claimed is:

1. A polymer having the following structure:

POLY(-W-T)$_n$ wherein:

POLY is a four-arm, branched PEG having a molecular weight from 300 to 100,000 daltons and having a pentaerythritol core;

W is a linkage comprising an ester;

T is a succinimidyl ester; and n is four.

2. The polymer of claim 1, wherein the linkage comprising an ester is —O—$(CH_2)_{n'}$—$CO_2$—$(CH_2)_m$—, wherein n' is 1 to 5 and m is 2 to 5.

3. The polymer of claim 1, wherein the succinimidyl ester is —$CO_2$—succinimidyl.

4. A method of forming a coupled product, the method comprising reacting a polymer having the following structure: POLY(-W-T)$_n$, with an amine-containing molecule under conditions effective to couple the polymer to the amine-containing molecule to thereby form the coupled product, wherein:

POLY is a four-arm, branched PEG having a molecular weight from 300 to 100,000 daltons and having a pentaerythritol core;

W is a linkage comprising an ester;

T is a succinimidyl ester; and n is four.

5. The method of claim 4, wherein the linkage comprising an ester is —O—$(CH_2)_{n'}$—$CO_2$—$(CH_2)_m$—, wherein n' is 1 to 5 and m is 2 to 5.

6. The method of claim 4, wherein the succinimidyl ester is —$CO_2$—succinimidyl.

7. The method of claim 4, wherein the amine-containing molecule is a peptide.

8. The method of claim 4, wherein: the succinimidyl ester is —$CO_2$-succinimidyl; and the amine-containing molecule is a peptide.

9. A composition comprising the coupled product formed by the method of claim 4.

* * * * *